(12) United States Patent
Kolkowitz et al.

(10) Patent No.: US 10,197,497 B2
(45) Date of Patent: Feb. 5, 2019

(54) SENSOR FOR MEASUREMENTS USING JOHNSON NOISE IN MATERIALS

(71) Applicant: President and Fellows of Harvard College, Cambridge, MA (US)

(72) Inventors: Shimon Jacob Kolkowitz, Cambridge, MA (US); Arthur Safira, Somerville, MA (US); Alexander A. High, Allston, MA (US); Robert C. Devlin, Abington, PA (US); Soonwon Choi, Cambridge, MA (US); Quirin P. Unterreithmeier, Cambridge, MA (US); David Patterson, Somerville, MA (US); Alexander S. Zibrov, Cambridge, MA (US); Vladimir E. Manucharyan, College Park, MD (US); Mikhail D. Lukin, Cambridge, MA (US); Hongkun Park, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/547,092

(22) PCT Filed: Jan. 29, 2016

(86) PCT No.: PCT/US2016/015710
§ 371 (c)(1),
(2) Date: Jul. 28, 2017

(87) PCT Pub. No.: WO2016/190920
PCT Pub. Date: Dec. 1, 2016

(65) Prior Publication Data
US 2018/0275057 A1    Sep. 27, 2018

Related U.S. Application Data

(60) Provisional application No. 62/109,271, filed on Jan. 29, 2015.

(51) Int. Cl.
*G01N 21/64* (2006.01)
*G01B 11/14* (2006.01)
*G01R 27/02* (2006.01)
*G01K 11/00* (2006.01)

(52) U.S. Cl.
CPC ......... *G01N 21/6408* (2013.01); *G01B 11/14* (2013.01); *G01K 11/00* (2013.01); *G01R 27/02* (2013.01)

(58) Field of Classification Search
CPC ........................... G01N 21/6408; G02B 11/14
See application file for complete search history.

(56) References Cited

U.S. PATENT DOCUMENTS

2014/0014171 A1    1/2014 Alam et al.

FOREIGN PATENT DOCUMENTS

CN         100469682 C    3/2009
WO    WO-2014/051886 A1   4/2014
(Continued)

OTHER PUBLICATIONS

International Search Report and Written Opinion issued by the U.S. Patent and Trademark Office for the International Application No. PCT/US2016/015710 dated Nov. 18, 2016 (7 pages).
(Continued)

*Primary Examiner* — Michael C Bryant
(74) *Attorney, Agent, or Firm* — Wilmer Cutler Pickering Hale and Dorr LLP

(57) ABSTRACT

A method of making measurements includes providing a sensor with at least one solid state electronic spin; irradiating the sensor with radiation from an electromagnetic radiation source that manipulates the solid state electronic spins to produce spin-dependent fluorescence, wherein the spin-dependent fluorescence decays as a function of relaxation time; providing a target material in the proximity of the sensor, wherein, thermally induced currents (Johnson noise)
(Continued)

present in the target material alters the fluorescence decay of the solid state electronic spins as a function of relaxation time; and determining a difference in the solid state spins spin-dependent fluorescence decay in the presence and absence of the target material and correlating the difference with a property of the sensor and/or target material.

21 Claims, 16 Drawing Sheets

(56) References Cited

FOREIGN PATENT DOCUMENTS

| WO | WO-2014/165505 A1 | 10/2014 |
|---|---|---|
| WO | WO-2014/165845 A1 | 10/2014 |

OTHER PUBLICATIONS

Kolkowitz, S., et al., "Probing magnetic noise near a conductor with a single spin qubit," Abstract Poster from: 2013 Joint Meeting of the APS Division of Atomic, Molecular & Optical Physics and the CAP Division of Atomic, Molecular & Optical Physics, Canada, vol. 58, No. 6, Monday-Friday, Jun. 3-7, 2013; Quebec City, Canada, 2 pages.

Kolkowitz, Shimon, "Nanoscale sensing with solid state spin qubits," University of Washington ABC Physics Seminar Presentation, 61 pages (Oct. 16, 2014).

Lin, Y.-J. et al., "Impact of the Casimir-Polder Potential and Johnson Noise on Bose-Einstein Condensate Stability near Surfaces," Physical Review Letters, vol. 92, 4 pages (Feb. 6, 2004).

SENSOR FOR MEASUREMENTS USING JOHNSON NOISE IN MATERIALS

RELATED APPLICATIONS

This Application is a national Stage Entry of PCT International Application No. PCT/US2016/15710 filed Jan. 29, 2016, which claims priority to U.S. Patent Application No. 62/109,271, filed Jan. 29, 2015, the contents of which are incorporated herein by reference in their entirety.

STATEMENT OF GOVERNMENT RIGHTS

This invention was made with government support under Grant No. HR0011-111-C-0073 awarded by the Defense Advanced Research Projects Agency (DARPA), Grant No. PHY-1125846 awarded by National Science Foundation (NSF), Grant No. 5710003324 awarded by Army Research Office (ARO), and Grant No. 5710003095 awarded by NSF. The government has certain rights in this invention.

BACKGROUND

Understanding electron transport, dissipation, and fluctuations at sub-micron length scales is critical for the continued miniaturization of electronic and optical devices, as well as atom and ion traps, and for the electrical control of solid-state quantum circuits. While it is well-known that electronic transport in small samples defies the conventional wisdom associated with macroscopic devices, resistance-free transport is difficult to observe directly. Most of the measurements demonstrating these effects make use of Ohmic contacts attached to sub-micron scale samples and observe quantized but finite resistance corresponding to the voltage drop at the contact of such a system with a macroscopic conductor. Techniques for non-invasive probing of electron transport are required because they can provide insights into electronic dynamics at small length scales.

SUMMARY OF INVENTION

In an aspect, a method of making measurements, including, providing a sensor with at least one solid state electronic spin; irradiating the sensor with radiation from an electromagnetic radiation source that manipulates the solid state electronic spins to produce spin-dependent fluorescence, wherein the spin-dependent fluorescence decays as a function of relaxation time; providing a target material in the proximity of the sensor, wherein, thermally induced currents (Johnson noise) present in the target material alters the fluorescence decay of the solid state electronic spins as a function of relaxation time; and determining a difference in the solid state spins spin-dependent fluorescence decay in the presence and absence of the target material and correlating the difference with a property of the sensor and/or target material.

In some embodiments, the property of the target material measured is localized at a length scale of 10-100 nm. In some other embodiments, the property measured is the resistance values within the target material. In some other embodiments, the property measured is the temperature of the of the target material.

In some embodiments, the property measured is the distance of the target material from the surface of the sensor.

In some embodiments, the property measured is the distance of the solid state electronic spins from the surface of the sensor.

In some embodiments, the sensor comprises a diamond crystal lattice. In some other embodiments, the solid state electronic spins comprises a defect in the diamond crystal lattice. In some other embodiment, the defect comprises a nitrogen vacancy center in a diamond crystal lattice.

In some embodiments, the electromagnetic radiation source is a laser. In some embodiments, the laser source emits light having wavelength of about 532 nanometers.

In some embodiments the target material is in contact with the sensor. In some other embodiments, the target material is not in contact with the sensor.

In some embodiments, the target material is a conductive material. In some embodiments, the target material is a metal. In some embodiments, the target material is silver. In some embodiments, the target material is copper.

In some embodiments, the target material is a single crystal. In some embodiments, the target material is polycrystalline.

In some embodiments, the target material is a conductive polymer.

BRIEF DESCRIPTION OF FIGURES

The following figures are provided for the purpose of illustration only and are not intended to be limiting.

FIGS. 5A-5B illustrate single-crystal AFM and TEM characterization according to one or more embodiments in which FIG. 5A is AFM image of a typical single-crystal silver surface grown for this work. The scan indicates a ~1 nm RMS roughness over a 4 μm×4 μm range, thus allowing for good diamond-silver contact; and FIG. 5B is a TEM image of a typical silver sample, where the growth direction is from left to right and the silver is capped with a titanium capping layer resulting in the brighter region on the right of the image. The image reveals single-crystallinity of the silver up to the surface.

FIG. 6B shows EBSD data for the same size region for single-crystal silver. No grain boundaries are visible; and FIG. 6C is the color scale conversion legend to map color to silver crystal orientation.

FIGS. 7A and 7B illustrate AFM and profilometer characterization of diamond surface according to one or more embodiments in which FIG. 7A is an AFM image of the surface of the diamond used for the single-crystal silver measurements and the scan indicates a ~1 nm RMS roughness over a 10 μm×10 μm range, thus allowing for good diamond-silver contact; and FIG. 7B is a profilometer scan of the surface of the diamond sample.

FIGS. 8A-8C show a silica ramp fabrication procedure according to one or more embodiments, in which FIGS. 8A and 8B show that following a 5 nm uniform CVD pre-deposition of $SiO_2$, a silica layer of gradually increasing thickness is fabricated on a diamond sample by placing a raised coverslip (raised ~300 μm) over the diamond, and growing the silica layer via an anisotropic CVD process; and FIG. 8C shows that a final 60 nm layer of silver is deposited on the ramp, so that NV centers at different points along the diamond are different distances away from the silver film.

FIGS. 11A-11D show NV decay rates near single-crystal silver with non-local fits according to one or more embodiments, in which FIG. 11A shows data for an NV in the same region (region A) as the NV in FIG. 4B (The extracted distance from the fit is z=33±2 nm. This was the smallest extracted distance observed for the single-crystal silver measurements.); FIG. 11B shows data for an NV in region B, where NVs are farther away from the silver film than in region A (The extracted distance from the fit is z=88±2 nm); FIG. 11C shows data for an NV in region C, where the largest separation between the NV and the metal film is expected (The extracted distance is z=141±4 nm); and FIG. 11D shows the same data as in FIG. 4D, measured $T_1$ versus extracted distance for two temperatures, 103 K (top) and 27 K (bottom), color coded by sample region (blue triangles in region A, pink squares in region B, gray circles in region C).

DETAILED DESCRIPTION

Figure 1A:
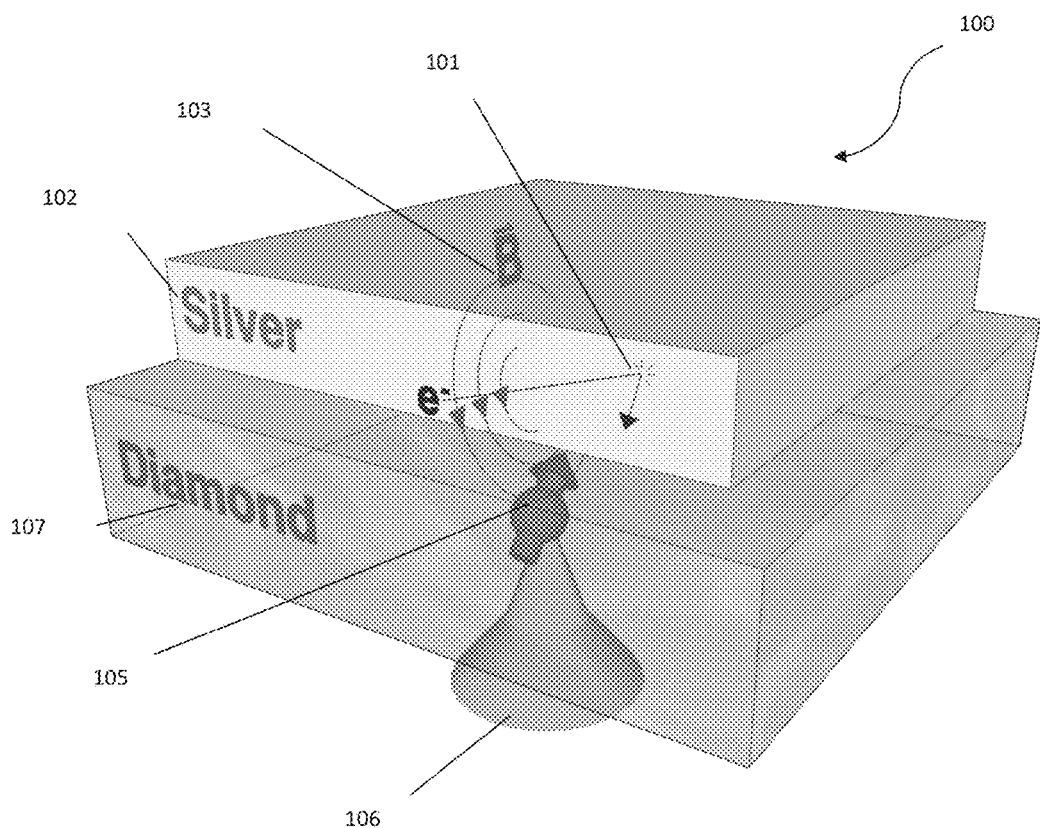
FIG. 1A illustrates the thermally induced motion of electrons 101 in silver 102, which generates fluctuating magnetic fields 103, which are detected using the spin of a single nitrogen vacancy center (NV) 105. The spin of the NV is polarized by an electromagnetic radiation source such as a laser 106 and read out through the back side of the diamond 107.

A method of making measurements using thermally induced currents, known as Johnson noise, is described. Johnson noise is the electronic and magnetic noise generated by the thermal agitation of the charge carriers, such as electrons, inside a material at equilibrium. The interaction of the magnetic Johnson noise with a sensor having solid state spins with spin-dependent fluorescence is used for measurement of properties of a sensor and/or target material.

When the sensor is irradiated with an electromagnetic radiation, the solid state spins absorb energy and emit fluorescence with a characteristic relaxation time that can be measured. However, the relaxation time of the solid state spin is altered when a target material with magnetic Johnson noise is brought in the proximity of the solid state spin. Among other parameters, the difference in the relaxation time of the solid state spin's spin-dependent fluorescence is correlated with the distance between the target material and the surface of the sensor, the temperature of the target material, and the resistance of the target material.

In an aspect, a method of making measurements, including providing a sensor with at least one solid state electronic spin; irradiating the sensor with radiation from the electromagnetic radiation source manipulates the solid state electronic spins to produce spin-dependent fluorescence, wherein the spin-dependent fluorescence decays as a function of relaxation time; providing a target material in the proximity of the sensor, wherein, thermally induced currents (Johnson noise) present in the target material alter the fluorescence decay of the solid state electronic spins as a function of relaxation time; and determining a difference in the solid state spins spin-dependent fluorescence decay in the presence and absence of the target material and correlating the difference with a property of the sensor and/or target material.

Currently, techniques do not exist to measure properties such as temperature and resistance of materials at resolutions in the length scale of 10-100 nm. Advantageously, using the method disclosed here enables the measurement of properties of the target material at a localized length scales of 10-100 nm. In some embodiments, the method is used for measuring the resistance values within the target material. In some other embodiments, the method is used for measuring the temperature of the target material.

In some embodiments, the method is used for measuring the distance of the target material from the surface of the sensor. In some embodiments, the method is used for measuring the distance of the solid state electronic spins from the surface of the sensor.

In some embodiments, the target material is a conductive material. Conductive materials such as metals can be used as target materials as the magnetic Johnson noise associated with these is large and can interact effectively with the solid state spins as described above. In some embodiments, the target material is silver. In another embodiment, the target material is copper. In yet another embodiment, the target material is a conductive polymer. In some other embodiments, the target material is a single crystal. In some other embodiments, the target material is polycrystalline.

In some embodiments, the sensor is a high purity diamond. In some other embodiments, the solid state electronic spin system is a NV spin. A NV spin in diamond is a crystallographic defect in the structure of a diamond, e.g., an empty position in a diamond's lattice. The NV spin is found as a defect in the lattice structure of a single crystal diamond. The NV impurity is based in the lattice of carbon atoms, where two adjacent sites are altered such that one carbon atom is replaced with a nitrogen atom and the other space is left vacant. The vacancies may interact with interstitial atoms, such as nitrogen, and may act as color centers by absorbing visible light. NV defects are visible as red spots when illuminated by a laser of the appropriate color. In some embodiments, the proximal NV spin is located about 5 nm to 50 nm below the diamond surface. In some other embodiments, the NV spin is located at about 2 to 50 nm, or 2 to 100 nm, or 1 to 100 nm or 1 to 200 nm, or 1 to 500 nm below the diamond surface.

In an aspect, the method includes use of the electromagnetic fluctuations associated with Johnson noise close to a conducting surface, which can be directly linked to the dielectric function at similar length scales, providing a non-invasive probe of electronic transport inside the metal. Advantageously, in some embodiments, measurements over a range of distances, such as 20-200 nm and temperatures, such as 10-300 K are possible.

In some embodiments, the target material is in contact with the sensor. In some other embodiments, the target material is not in contact with the sensor. Advantageously, when the target material is not in contact with the sensor, measurements in cryogenic conditions are more reliable and accurate since the sensor does not act as a heat sink causing errors in measurement.

Figure 1B:
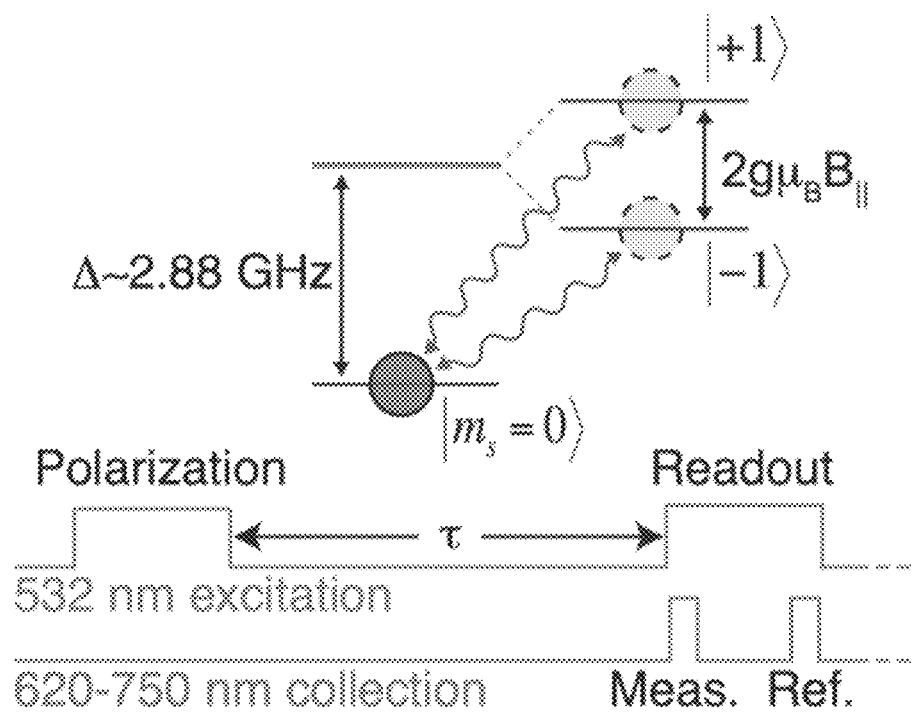
FIG. 1B illustrates that the NV spin is polarized into $|m_s=0\rangle$ state using a green laser pulse. Spin relaxation into the $|m_s=\pm 1\rangle$ states is induced by magnetic field noise at 2.88 GHz. After wait time $\tau$ the population left in $|0\rangle$ is read out by spin-dependent fluorescence. All measurements shown were performed at low magnetic fields ($\Delta \gg g\mu_B B\|\hbar$)

In an aspect, the method makes use of the electronic spin associated with NV defect centers defect centers in diamond to study the spectral, spatial, and temperature dependence of Johnson noise emanating from conductors. The magnetic Johnson noise results in a reduction of the spin lifetime of individual NV electronic spins, thereby allowing a probe of the intrinsic properties of the conductor non-invasively over a wide range of parameters. In some embodiments, individual, optically resolvable, NV centers are implanted ~15 nm below the surface of a ~30-μm thick diamond sample. A silver film is then deposited on or positioned on the diamond surface. FIG. 1A illustrates the thermally induced motion of electrons 101 in silver 102, which generates fluctuating magnetic fields 103, which are detected using the spin of a single NV 105. The spin of the NV is polarized by an electromagnetic radiation source such as a laser 106 and read out through the back side of the diamond 107. The spin sublevels $|m_s=0\rangle$ and $|m_s=\pm 1\rangle$ of the NV electronic ground state exhibit a zero-field splitting of $\Delta=2\pi\times 2.88$ GHz. The relaxation rates between the $|0\rangle$ and $|\pm 1\rangle$ states provide a sensitive probe of the magnetic field noise 103 at the transition frequencies $\omega_\pm=\Delta\pm 2g\mu_B B_\parallel/\hbar$, where $B_\parallel$ is the magnetic field along the NV axis. In an embodiment, as illustrated in FIG. 1B, the NV spin is polarized into $|m_s=0\rangle$ state using a green laser pulse. Spin relaxation into the $|m_s=\pm 1\rangle$ states is induced by magnetic field noise at ~2.88 GHz. After wait time τ the population left in $|0\rangle$ is read out by spin-dependent fluorescence. All measurements shown were performed at low magnetic fields ($\Delta\gg g\mu_B B_\parallel/\hbar$).

Figure 1C:
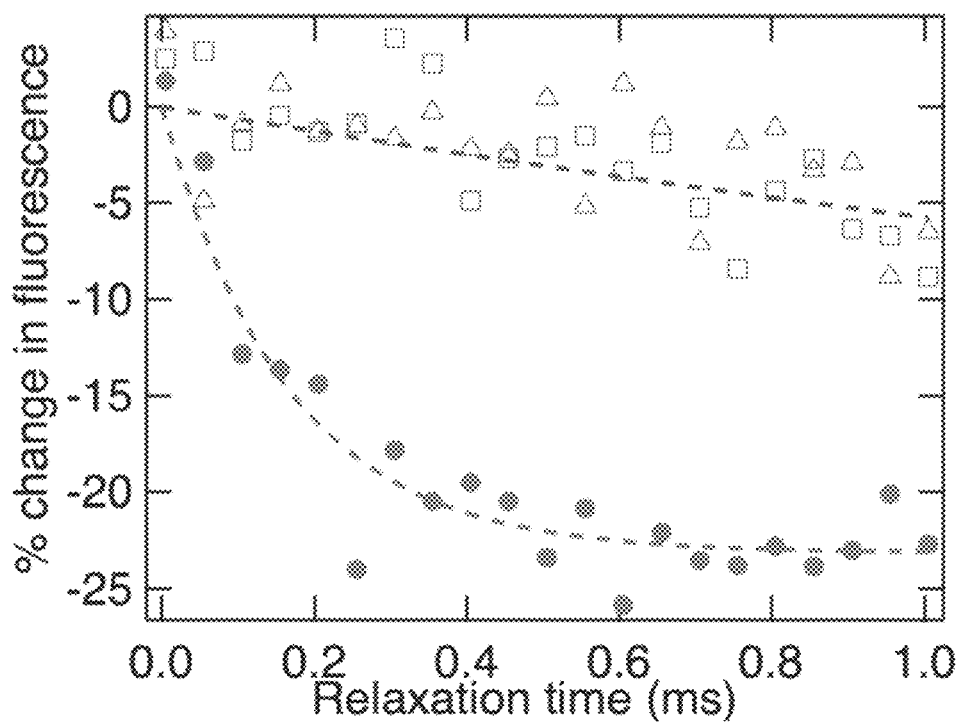
FIG. 1C illustrates, the spin relaxation data for the same single shallow implant NV described in FIG. 1B, before silver deposition (open blue squares), with silver deposited (red circles), and after the silver has been removed (open blue triangles)
Figure 1D:
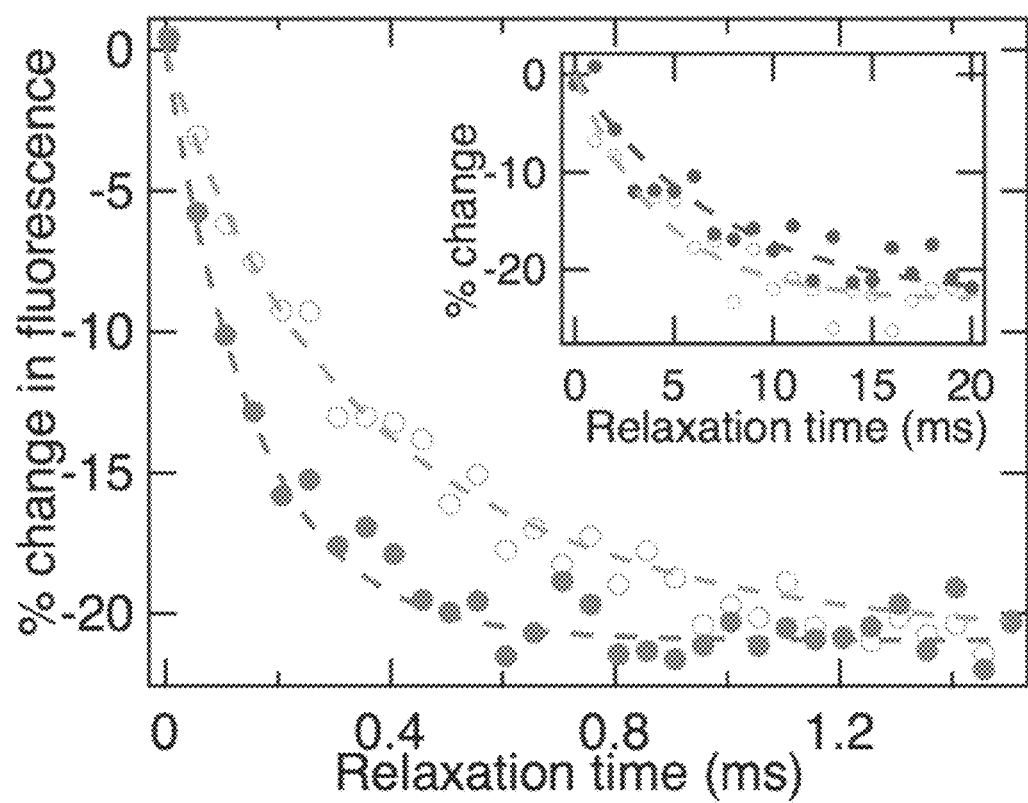
FIG. 1D illustrates, spin relaxation for a single native NV in bulk diamond in the $|m_s=0\rangle$ state (blue circles), and in the $|m_s=-1\rangle$ state (open light blue circles)

FIG. 1C illustrates, the spin relaxation data for the same single shallow implant NV 105 described in FIG. 1B, before silver deposition (open blue squares), with silver deposited (red circles), and after the silver has been removed (open blue triangles). The impact of Johnson noise emanating from a polycrystalline silver film deposited on the diamond surface, as shown in FIG. 1C, is evident when comparing the relaxation of a single NV spin below the silver (red circles) to the relaxation of the same NV prior to film deposition and after removal of the silver (open blue squares and triangles, respectively).[1] At room temperature and in the absence of external noise, the spin lifetime is limited by phonon-induced relaxation to $T_1^{ph}\approx 4$ ms. With the silver nearby, the lifetime of the $|m_s=0\rangle$ state is reduced to $T_1=165$ μs, which is attributed to the magnetic Johnson noise emanating from the film. FIG. 1D illustrates spin relaxation data for a single NV close to silver film prepared in the $|m_s=0\rangle$ state (red circles), and in the $|m_s=-1\rangle$ state (open orange circles). The inset of FIG. 1D illustrates, spin relaxation for a single native NV 105 in bulk diamond in the $|m_s=0\rangle$ state (blue circles), and in the $|m_s=-1\rangle$ state (open light blue circles). Comparing the lifetime of the $|0\rangle$ state, which has magnetic dipole allowed transitions to both of the $|\pm 1\rangle$ states, to that of the $|-1\rangle$ state, which can only decay directly to the $|0\rangle$ state verifies that the enhanced relaxation is due to magnetic noise as showing in FIG. 1D. Also, for relaxation induced by magnetic noise, the $|-1\rangle$ state has approximately twice the lifetime of the $|0\rangle$ state. This is in contrast to the observed lifetimes when limited by phonon-induced relaxation (Inset, FIG. 1D), where the $|0\rangle$ and $|\pm 1\rangle$ states have almost identical lifetimes. In what follows, defines $T_1$ as the lifetime of the $|m_s=0\rangle$ state.

Figure 2A:
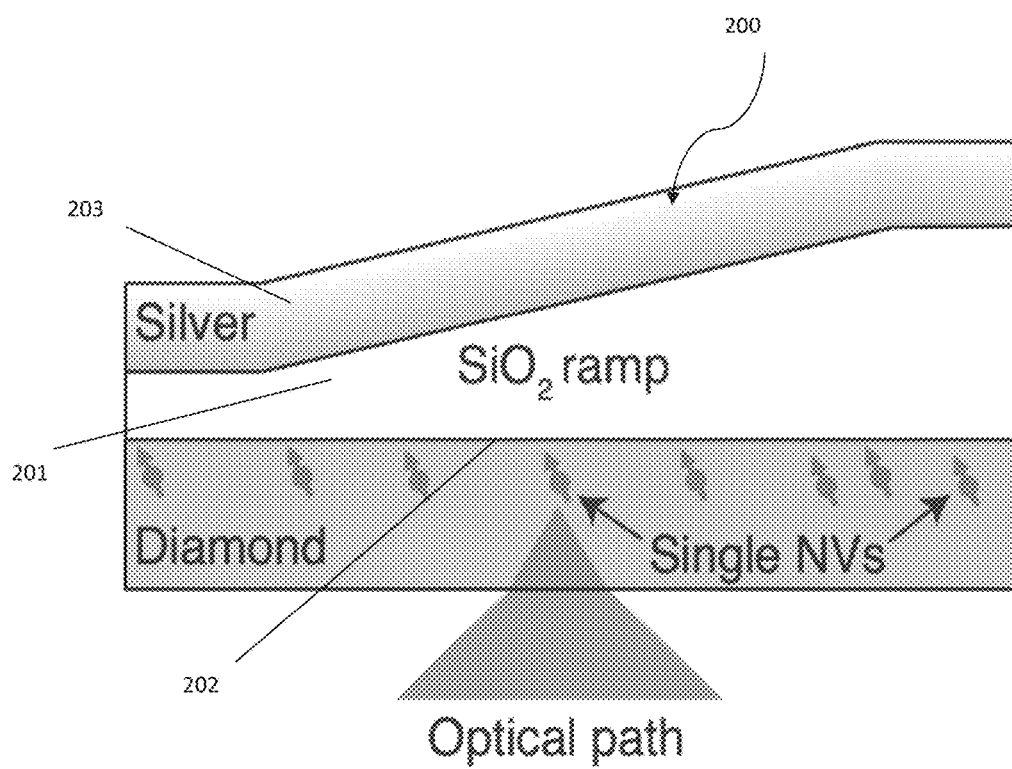
FIG. 2A. illustrates a gradual ramp of slope ~0.2 nm/micron of $SiO_2$ 201, grown on a diamond surface 202, followed by a 60 nm silver (Ag) film 203.
Figure 2B:
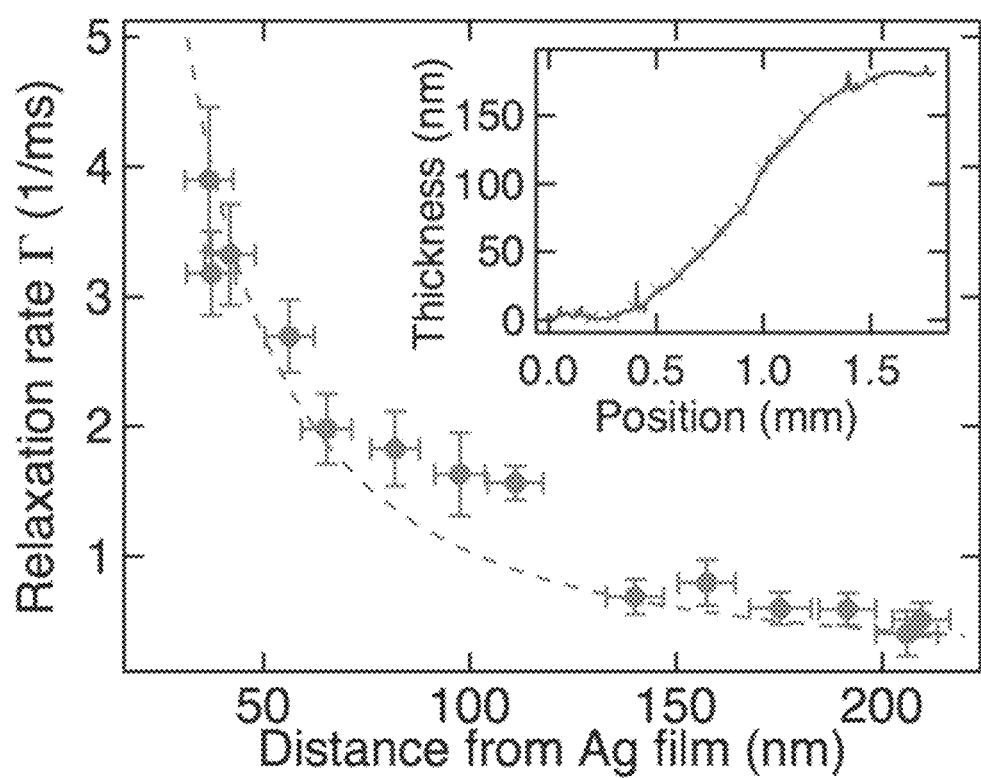
FIG. 2B illustrates the NV relaxation rate measured as a function of the position along the ramp shown in FIG. 2A which is them converted into the distance to the film. At each point, 5-10 NV centers are measured, and the minimum measured rate is plotted (red circles). The red dashed line shows the expected relaxation rate with no free parameters after accounting for the finite silver film thickness. The thickness of the $SiO_2$ layer as a function of lateral position along the diamond sample (blue curve) and the positions along the sample where the measurements were taken (red crosses), are show in the inset of FIG. 2B.

To test the scaling of Johnson noise with distance (d) to the metal, a layer of $SiO_2$ is deposited on the diamond surface with a gradually increasing thickness. FIG. 2A. illustrates a gradual ramp of slope ~0.2 nm/micron of $SiO_2$ 201, grown on a diamond surface 202, followed by a 60 nm silver (Ag) film 203. FIG. 2B illustrates the NV relaxation rate measured as a function of the position along the ramp shown in FIG. 2A which is them converted into the distance to the film. At each point, 5-10 NV centers are measured, and the minimum rate with no free parameter is plotted (red circles). The red dashed line shows the expected relaxation rate with no free parameters after accounting for the finite silver film thickness. The thickness of the SiO$_2$ layer as a function of lateral position along the diamond sample (blue curve) and the positions along the sample where the measurements were taken (red crosses), are show in the inset of FIG. 2B. Another 60-nm polycrystalline silver film is deposited on top of the SiO$_2$. The conductivity of the silver film is measured to be 2.9×10$^7$ S/m at room temperature. By measuring the relaxation rates $\Gamma=1/T_1$ of individual NVs at different positions along the SiO$_2$ ramp the distance dependence of the noise can be extracted as shown in FIG. 2B, with the uncertainty in the distance dominated by the variation in the implanted depth of the NVs (taken to be 15±10 nm). To ensure that the measured rates are Johnson-noise limited, we measure the spin relaxation of 5-10 randomly selected NVs per location along the ramp, and plot the minimum observed rate at each location. The magnitude of the noise increases as the NVs approach the silver surface.

To investigate the dependence of the noise on temperature and conductivity, a 100-nm polycrystalline silver film on a diamond sample was deposited and the $T_1$ of a single NV beneath the silver over a range of temperatures (~10-295 K) was measured. The measured relaxation rate for a single NV near the silver increased with temperature for thermal noise, as shown by the red circles in FIG. 3A. However, it was observed that the scaling was non-linear. One skilled in the art would recognize that the conductivity of the silver film is also a function of temperature, and that the magnitude of the thermal currents in the silver depend on the conductivity. To account for this effect, a four point resistance measurement of the silver film was performed to determine the temperature dependence of the bulk conductivity of the silver film. The results of the four point resistance measurement are show in FIG. 3B. FIG. 3B illustrates the conductivity of the 100 nm thick polycrystalline silver film deposited on the diamond surface measured as a function of temperature. The inset of FIG. 3B shows grain boundaries within the polycrystalline silver film, imaged using electron backscatter diffraction (EBSD). In some embodiments, the average grain diameter is 140 nm, with a standard deviation of 80 nm.

To analyze the dependence of the NV spin relaxation rate on distance, temperature, and conductivity, a model in which an electronic spin-½ qubit with Larmor frequency $\omega_L$ is positioned at a distance d from the surface of a metal was used. For silver at room temperature the skin depth at $\omega_L$ is δ≈1 μm; consequently when d<100 nm, the "quasi-static" limit d<<δ applies. The thermal limit $k_B T>>\hbar\omega_L$ is valid for all temperatures in this disclosure. In this regime the magnetic noise spectral density perpendicular to the silver surface is given by $$S_B^z = \frac{\mu_o^2}{16\pi} \frac{k_B T \sigma}{d}, \quad (1)$$

where σ is the temperature-dependent conductivity of the metal as defined by the Drude model. This scaling can be intuitively understood by considering the magnetic field generated by a single thermal electron in the metal at the NV position, $B_o=(\mu_o e v_{th})/(4\pi d^2)$, where the thermal velocity $v_{th} \propto \sqrt{k_B T/m_e}$, $m_e$ is the effective mass of electrons in silver and e is the electron charge. In the limit d<<δ screening can be safely ignored, and the NV experiences the magnetic field spectrum arising from N independent electrons in a volume V, $S_B \propto V n \langle B_o \rangle^2 \tau_c$, where n is the electron density and $\tau_c$ is the correlation time of the noise, given by the average time between electron scattering events, $\tau_c = l/v_F$, where l is the electron mean free path and $v_F$ is the Fermi velocity. Recognizing that the NV is sensitive to the motion of electrons within a sensing volume $V \propto d^3$, we arrive at the scaling given by Eq. 1, with $\sigma=(ne^2\tau_c)/(m_e)$. Applying Fermi's golden rule and accounting for the orientation and spin-1 of the NV yields the relaxation rate for the $|m_s=0\rangle$ state $$\Gamma = \frac{1}{T_1} = \frac{3 g^2 \mu_B^2}{2\hbar^2} S_B^z \left(1 + \frac{1}{2}\sin^2(\theta)\right), \quad (2)$$

where g≈2 is the electron g-factor, $\mu_B$ is the Bohr magneton, and θ≈54.7" is the angle of the NV dipole relative to the surface normal vector. In FIG. 2B the inverse scaling with distance d predicted by Equation 1 is clearly evident for NVs very close to the silver. At distances comparable to the silver film thickness Equation 1 is no longer valid, but we recover excellent agreement with the no-free-parameters prediction of Eq. 2 by including a correction for the thickness of the silver film (red dashed line in FIG. 2B), which is measured independently. The measured relaxation rates as a function of temperature are also in excellent agreement with the predictions of Equation 2 (red dashed line in FIG. 3A), while the extracted distance of 31±1 nm is consistent with the expected depth.

Figure 3B:
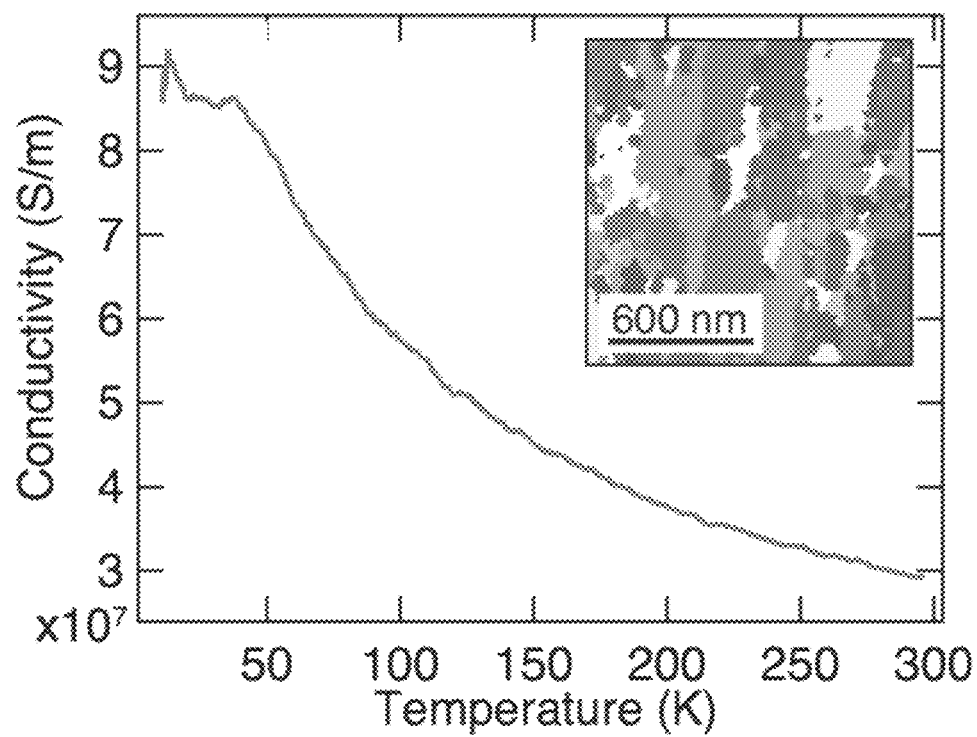
FIG. 3B illustrates the conductivity of the 100 nm thick polycrystalline silver film deposited on the diamond surface measured as a function of temperature. The inset of FIG. 3B shows grain boundaries within the polycrystalline silver film, imaged using electron backscatter diffraction (EBSD)
Figure 4A:
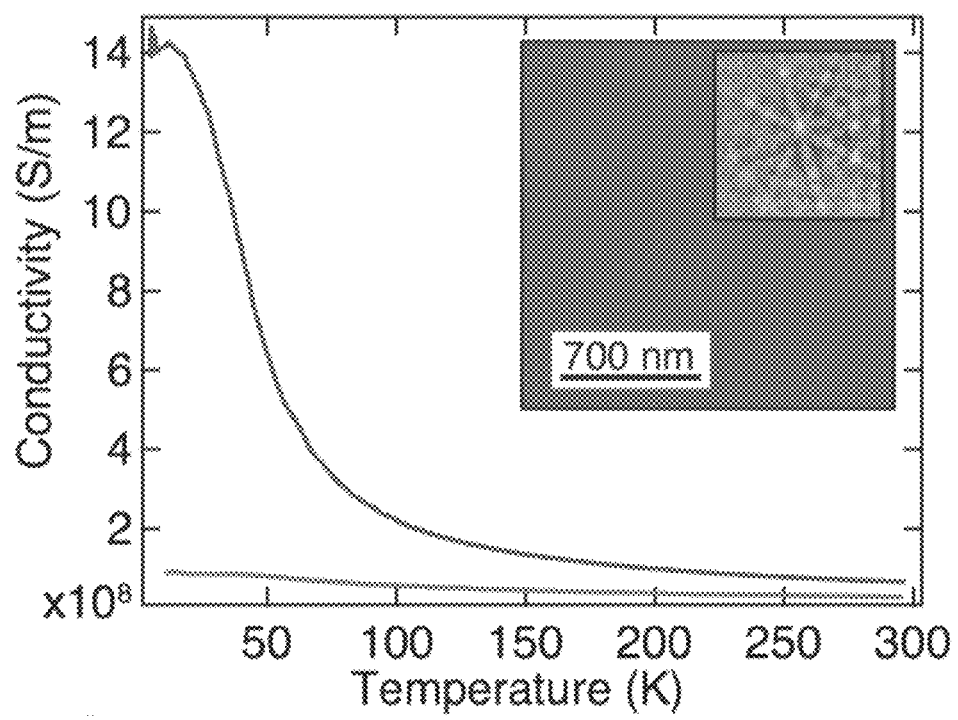
FIG. 4A illustrates, measured conductivity of single-crystal (blue curve) and polycrystalline (red curve, same as FIG. 3B) silver as a function of temperature. (Inset) Electron backscatter diffraction image of the single-crystal silver film showing no grain boundaries, and the observed diffraction pattern.
Figure 4B:
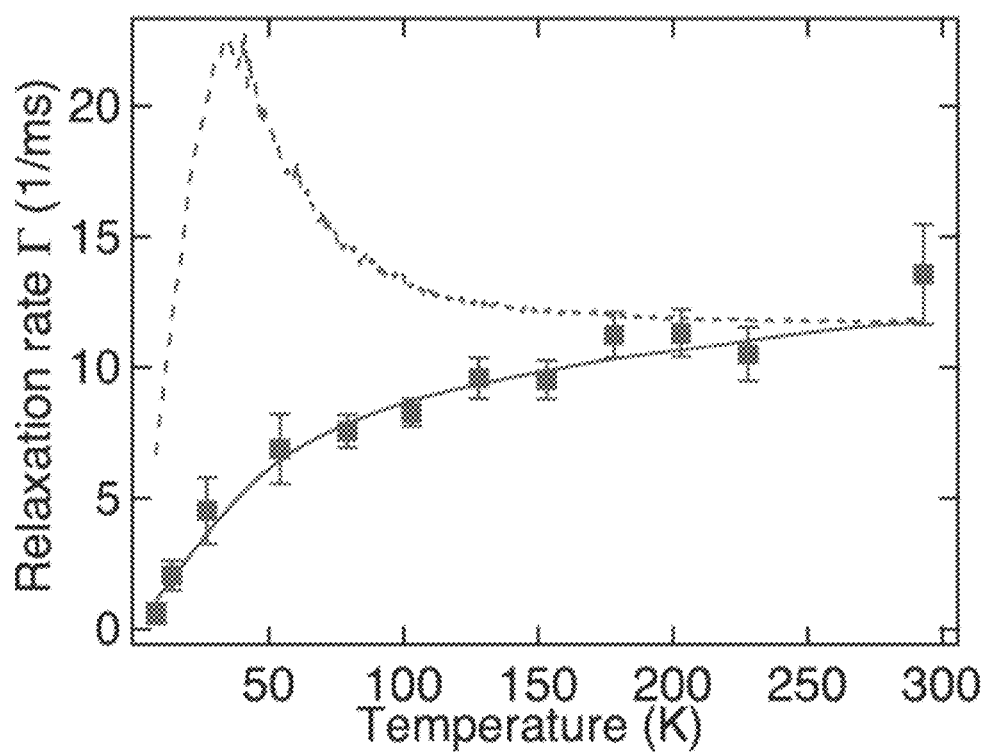
FIG. 4B illustrates, relaxation of a single NV spin under single-crystal silver as a function of temperature (blue squares). Equation 2 is fit to the data from 200-295 K (blue dashed line). A non-local model is fit to the data (blue solid line), the extracted distance between the NV and the silver surface is 36±1 nm.

Remarkably, very different results were obtained when the polycrystalline film was replaced with single-crystal silver. A 1.5-μm thick single-crystal silver film grown by sputtering onto silicon was placed in contact with the diamond surface. FIG. 4A illustrates, measured conductivity of single-crystal (blue curve) and polycrystalline (red curve, same as FIG. 3B) silver as a function of temperature. (Inset) Electron backscatter diffraction image of the single-crystal silver film showing no grain boundaries, and the observed diffraction pattern. FIG. 4B presents the measured relaxation rate as a function of temperature for an NV in a region in direct contact with the single-crystal silver (blue squares). The dashed blue line corresponds to the temperature dependent rate predicted by Equation 2, which strongly disagrees with the experimental results. Specifically, because the measured silver conductivity increases faster than the temperature decreases in the range from room temperature down to 40 K, Equation 2 predicts the relaxation rate should increase as the temperature drops, peaking at 40 K and then dropping linearly with temperature once the conductivity saturates. Instead, the T1 of the NV consistently increases as the temperature drops, implying that at lower temperatures the silver produces considerably less noise than expected from Equation 2. We observe similar deviation from the prediction of Equation 2 for all 23 NVs measured in the vicinity of the single-crystal silver.

Figure 4C:
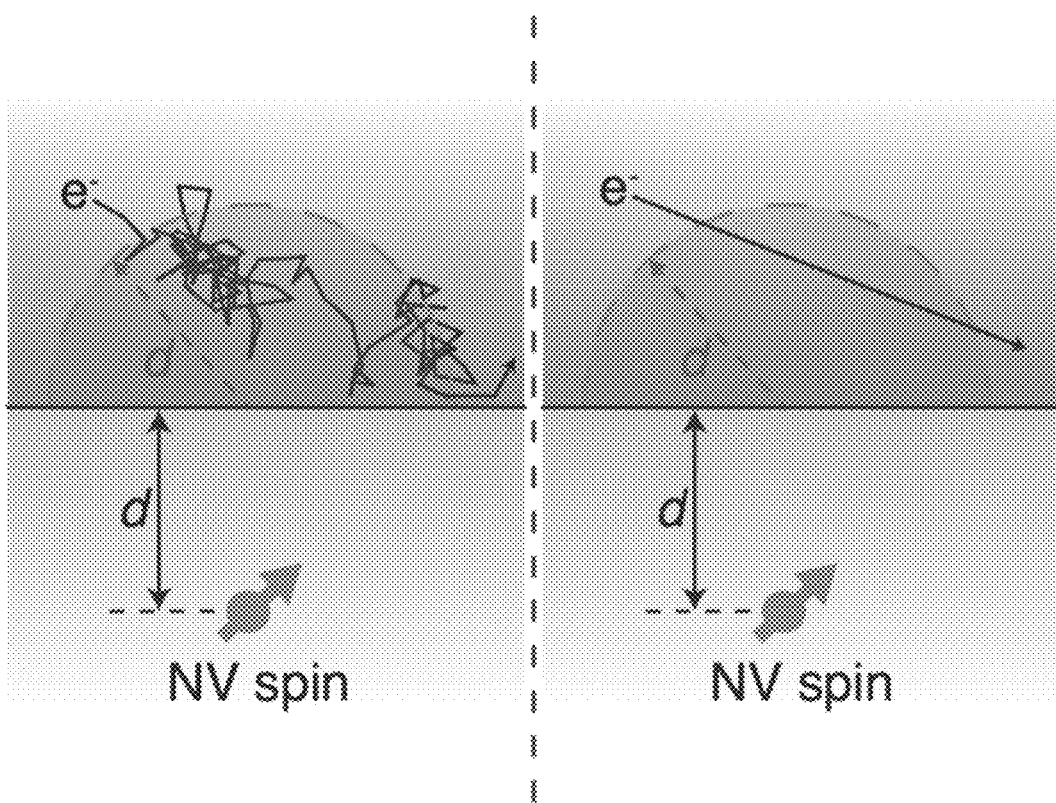
FIG. 4C is a schematic illustrating the relevant limits, where the noise is dominated by diffusive electron motion (left, l<<I), and ballistic motion (right, l>>d)

To analyze these observations, it is noted that the conventional theoretical approach resulting in Equation 2 treats the motion of the electrons in the metal as entirely diffusive, using Ohm's law, J(r, t)=σE(r, t), to associate the bulk conductivity of the metal with the magnitude of the thermal currents. While accurately describing the observed relaxation rates next to the polycrystalline material, where the resistivity of the film is dominated by electron scattering off of grain boundaries (Inset, FIG. 3B), this assumption is invalid in the single-crystal silver film experiments, particularly at low temperatures. Here, the measured conductivity of the single crystal film indicate that the mean free path l is greater than one micron, significantly exceeding the sensing region determined by the NV-metal separation, and thus the ballistic motion of the electrons must be accounted for. Qualitatively, the correlation time of the magnetic noise in this regime is determined by the ballistic time of flight of electrons through the relevant interaction region $\tau_c \sim d/v_F$ (as illustrated in FIG. 4C). This results in a saturation of the noise spectral density and the spin relaxation rate as either the NV approaches the silver surface or as the mean free path becomes longer at lower temperatures, with the ultimate limit to the noise spectrum given by:

$$S_B^z \sim \frac{2\mu_0^2 k_B T}{\pi} \frac{n\varepsilon^2}{m_c v_F}. \qquad (3)$$

Figure 4D:
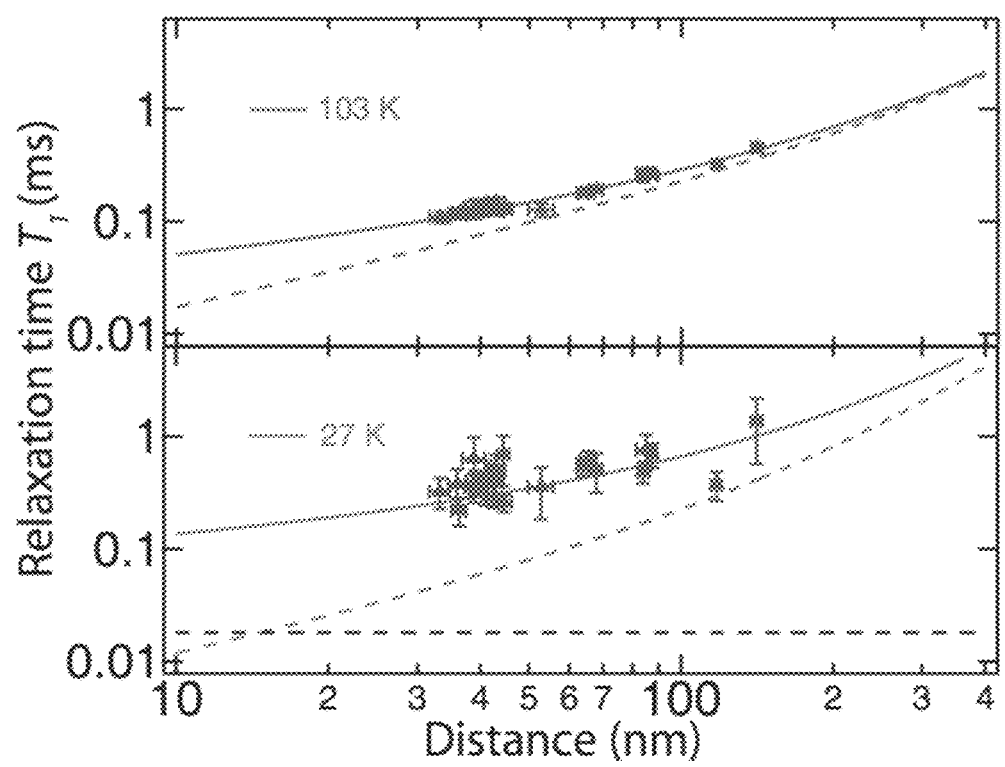
FIG. 4D illustrates the same data as shown in FIG. 4B for 23 NVs at varying distances from the film. The $T_1$ of each NV at 103 K (top) and 27 K (bottom) is plotted against the extracted depth (blue triangles). The non-local model (solid colored lines) saturates at a finite lifetime determined by Equation 3 (bottom, dashed black line), while the local model does not (dashed colored lines).

This regime of magnetic Johnson noise was analyzed theoretically using the Lindhard form non-local dielectric function for the metal modified for finite electron scattering times. Comparison of this model (solid line in FIG. 4B) to the data, with distance again as the only free parameter, yields excellent agreement for all 23 measured NVs. FIG. 4D shows the measured T1 times at 103 K and 27 K for each NV as a function of extracted distance (blue triangles). Of the 23 NVs measured, 15 are in a region of the diamond sample in direct contact with the silver. Excellent agreement between the non-local model (solid lines) and the data is observed for all 23 NVs at all 12 measured temperatures. Apparent in FIG. 4D is the saturation of the relaxation rate as the NV approaches the silver surface, and as the mean free path becomes longer at lower temperatures (dashed black line), as predicted by Equation 3.

While ballistic electron motion in nanoscale structures has previously been studied and utilized, our approach allows for non-invasive probing of this and related phenomena, and provides the possibility for studying mesoscopic physics in macroscopic samples. The combination of sensitivity and spatial resolution demonstrated here enables direct probing of current fluctuations in the proximity of individual impurities, with potential applications such as imaging of Kondo states and probing of novel two-dimensional materials, where our technique may allow for the spatially resolved probing of edge states. Likewise, it could enable investigation of the origin of 1/f flux noise by probing magnetic fluctuations near superconducting Josephson circuits. Finally, as Johnson noise presents an important limitation to the control of classical and quantum mechanical devices at small length scales, the present results demonstrate that this limitation can be circumvented by operating below the length scale determined by the electron mean free path.

The invention is illustrated in the following examples, which are for purposes of illustration only and not intended to be limiting of the invention.

1. Experimental Methods

The experiments were performed using 30 micron thick electronic grade diamonds grown, thinned, and polished by Element Six with a natural isotopic abundance of carbon. Shallow NV centers were generated through Nitrogen-14 implantation at 6 keV energy at a density of $2 \times 10^9/\text{cm}^2$, followed by annealing at 800° C. The single-crystal silver films were grown by sputtering at 300° C. onto a (111) oriented single-crystal silicon substrate, with a deposition rate of ~1.5 nm/s. The polycrystalline silver films were evaporated directly onto the diamond. A 5-nm layer of silica ($SiO_2$) was grown on the diamond surface prior to the metal deposition to preserve NV properties. Temperature dependence measurements were performed in a Montana Instruments closed cycle cryostat.

2, Fabrication and Metrology 2.1 Single-Crystal Silver Deposition and Characterization The single-crystalline silver films were grown using direct current plasma sputtering (AJA International Orion 3). The sputtering targets used were 99.99% pure silver (Kurt Lesker, Inc). Films were deposited onto prime-grade, degenerately doped (111)-Si wafers (0.0015-0.005 Ω-cm). The substrates were ultrasonically cleaned in acetone, followed by a 2:1 sulfuric acid:hydrogen peroxide solution to eliminate organics. The substrates were then immersed in 49% hydrofluoric acid for 10-15 seconds to remove any native oxide. Next, the substrates were rapidly transferred into the sputtering chamber and the chamber was pumped down to minimize re-oxidation of the surface. Upon reaching a base pressure of about $5 \times 10^{-7}$ Torr, the substrate was heated to 300° C. and silver was deposited at a rate of 1.5-1.7 nm/s.

Figure 5A:
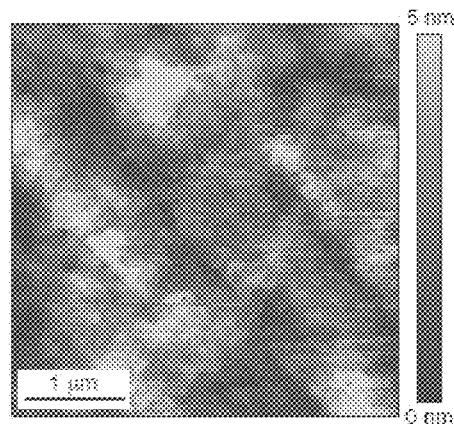
Figure 5B:
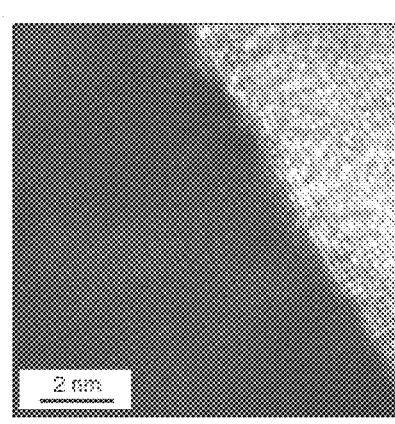

Following the growth, multiple characterization techniques were used to test the quality of the deposited films. The crystallinity and surface quality of the films were probed via transmission electron microscopy (TEM) and atomic force microscopy (see FIGS. 5A and 5B). The TEM scans confirm that the silver films are single-crystal, with lattice fringes apparent from the bulk to the surface. The AFM scans confirm that the films are ultra-smooth with typical root-mean-square roughness of ~1 nm. Consistent with the TEM scans and electron backscatter diffraction imaging (see below), no grain boundaries were observed within the 10 μm×10 μm scan region.

2.2 Characterization of Silver Film Grain Size

Figure 6A:
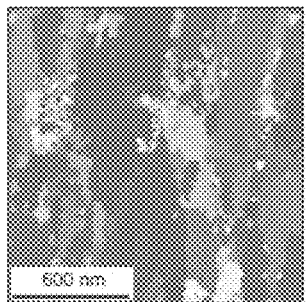
FIGS. 6A-6C show single-crystal and polycrystalline silver Inverse Pole Figures (IPF) according to one or more embodiments using electron backscatter diffraction imaging in an SEM to image the local crystal orientations of silver films, and measure the average grain size, in which FIG. 6A are data for a 2 μm×2 μm area of evaporated silver on 5 nm of $SiO^2$ on (100) silicon (the crystal variations along the direction perpendicular to the sample can cause mixed diffraction signals, and the crystal orientation fits in those regions have low confidence and result in an IPF with unphysical pixel-to-pixel variations in the crystal orientation (left region of image))
Figure 6B:
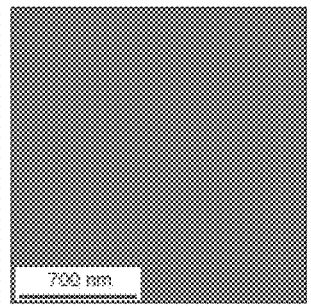
Figure 6C:
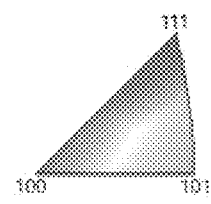

Crystal orientation and average grain size of the silver samples were measured with electron backscatter diffraction (EBSD). For the polycrystalline films a 100 nm film deposited on 5 nm of SiO2 on (100) silicon is used as a reference. In the insets of FIGS. 3 and 4, inverse pole figures of the electron backscatter diffraction data were post-processed to highlight grain boundaries. The areas in white are areas of large noise where the crystal orientation could not be discerned with high confidence, while the other colors indicate different crystal orientations. The inverse pole figures from which those images are derived are given in FIGS. 6A-6C. EBSD data of the polycrystalline silver film indicated a very granular film, with an average grain diameter of 140 nm and a standard deviation of 80 nm. Grain diameter was approximated by taking the diameter of the circle with the same area as each grain. For the single-crystal films, EBSD data indicated the sample is a single-crystal from nanometer to millimeter length scales, and confirmed a (111) exposed crystal surface for the single-crystal silver, as expected from the growth conditions.

2.3 Diamond Surface Characterization

Figure 7A:
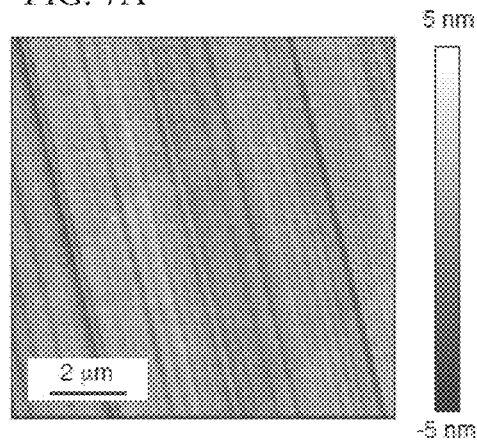
Figure 7B:
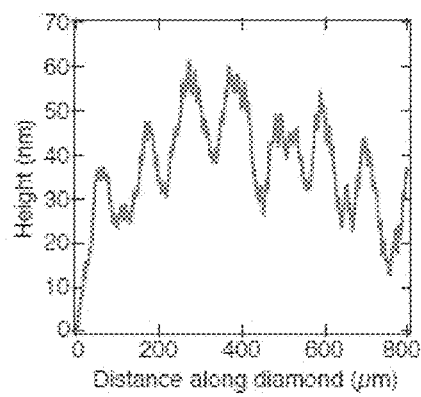

AFM and profilometer scans were performed on the implantation-side surface of the diamond used for the single-crystal silver measurements, as shown in FIGS. 7A and 7B. The diamond was found to have a local surface roughness of ~1 nm RMS over a 10 μm×10 μm range, and to have variations of ~10-20 nm peak to peak at the ~100 micron length scale across the entire sample. The NVs sampled from the spatial region over which the diamond was considered to be in contact with the silver were all within a single 40 μm×40 μm field of view.

2.4 Spacer Layer Fabrication for Distance Dependence Studies

Figure 8A:
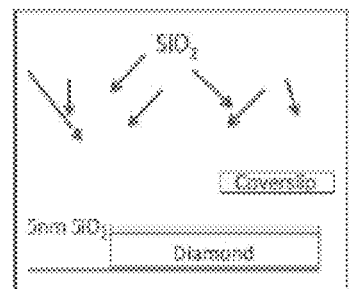
Figure 8B:
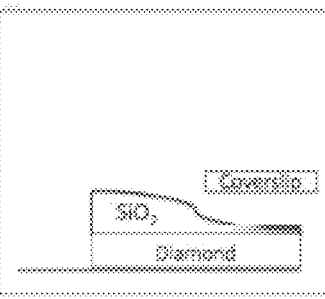
Figure 8C:
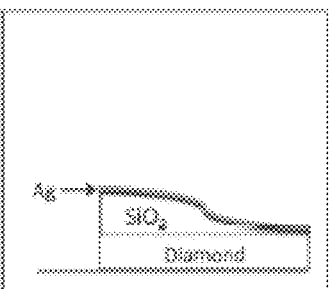

Distance-dependence studies of the noise were carried out by growing a spacer layer of $SiO_2$ between the evaporated silver metal and diamond. A 5-nm thick film of $SiO_2$ was first deposited via CVD on the diamond. A 100 μm thick sapphire slide was then placed ~300 μm above the surface of a diamond crystal-bonded to a silicon carrier wafer (see illustration in FIGS. 8A-8C.) The anisotropic CVD $SiO_2$ deposition results in a smooth ramp, as measured by a profilometer (See FIG. 2). A 60 nm film of silver was then deposited on the structure in an electron-beam evaporator.

2.5 Fabrication of Devices for Temperature-Dependent Studies

For the temperature dependence measurements under evaporated polycrystalline silver (FIG. 3), a 5 nm layer of silica was deposited onto the diamond via CVD growth, and a 100 nm layer of silver was then deposited onto the silica film.

The device used in this experiment was fabricated using optical contact bonding between the diamond and the single-crystal silver surfaces. The diamond sample was prepared for bonding by cleaning in a boiling 1:1:1 solution of nitric, sulfuric, and perchloric acids for at least one hour, directly prior to bonding. After growth, the single-crystal silver films were stored with a 50 nm capping layer of alumina to prevent surface oxidation. Directly prior to the bonding process, the alumina capping layer was stripped away in hydrofluoric acid. The diamond was then placed NV side down in contact with the freshly exposed silver surface. A drop of de-ionized water was placed on top of the diamond and allowed to wick in-between the diamond and the silver, and the diamond was lightly pressed against the silver from above, while the two samples were blow-dried with a nitrogen spray gun, leaving the diamond bonded directly to the silver surface. This procedure was performed in a cleanroom, with careful attention to the cleanliness of the tweezers and sample holders. The final device used in this experiment demonstrated very robust bonding between the diamond and the silver, and survived multiple thermal cycles from 300-10 K.

3. Johnson Noise Theory 3.1 Spin Decay Rate Near a Conducting Metallic Half-Space From Fermi's golden rule and the fluctuation-dissipation theorem, the decay rate from $|ms=0\rangle$ to $|ms=1\rangle$ for a spin-1 system at a distance z above the surface of a metal at temperature T, with level separation ω and magnetic dipole moment in the ith direction is then given by $$\Gamma_{0\to 1} = \frac{\mu^2}{\hbar^2}\coth\left(\frac{\hbar\omega}{2k_B T}\right) S_B^{ii}(z,\omega) \tag{S1}$$

where $$S_B^x(z,\omega) = S_B^y(z,\omega) = \tag{S2}$$
$$\frac{\hbar}{8\pi\epsilon_0 c^3}\text{Re}\int_0^\infty dp \frac{p(\omega^2 r^p(p) + (p^2c^2-\omega^2)r^s(p))}{\sqrt{\omega^2 - p^2 c^2}} e^{2iz\sqrt{\omega^2/c^2 - p^2}}$$

$$S_B^z(z,\omega) = \frac{\hbar}{4\pi\epsilon_0 c^2}\text{Re}\int_0^\infty dp \frac{p^3}{\sqrt{\omega^2/c^2 - p^2}} e^{2iz\sqrt{\omega^2/c^2-p^2}} r^s(p), \tag{S3}$$

and $r^p$ and $r^s$ denote the Fresnel Coefficients for plane waves incident on the material interface for p and s polarized light, respectively. We choose a coordinate system in which the z axis is perpendicular to the material interface; as $S_B^{\alpha\beta}$ is a diagonal tensor in this coordinate system, we drop one index and denote the diagonal elements by identifying $S_B^{ii}=S_B^i$. We have also assumed off-diagonal density matrix elements to be 0, $\rho_{ij}=\langle i|\rho|j\rangle=\Sigma\delta_{ij}$, consistent with $T_2^*$ of the NVs in our experiment being much faster than the population dynamics of system.

3.2 Reflection Coefficients

Explicitly, the reflection coefficients for a single material boundary are given by $$r^s(p) = \frac{k_1 - k_2}{k_1 + k_2} \tag{S4}$$

$$r^p(p) = \frac{\epsilon_2 k_1 - \epsilon_1 k_2}{\epsilon_2 k_1 + \epsilon_1 k_2} \tag{S5}$$

with $$k_1 = \sqrt{\epsilon_1 \omega^2/c^2 - p^2} \tag{S6}$$

$$k_2 = \sqrt{\epsilon_2 \omega^2/c^2 - p^2} \tag{S7}$$

where we have assumed $\mu_r \approx 1$ in all space, consistent with the materials used in this study. In the case of a spin above a metal, the above coefficients are valid when the thickness of the metal greatly exceeds the skin depth or when the spin-metal distance is much less than the thickness. To take into account the finite thickness of the film, the reflection coefficients take the form $$r^s(p) = \frac{k_1^2 - k_2^2}{k_1^2 + k_2^2 + 2ik_1 k_2 \cot(k_2 a)} \tag{S8}$$

$$r^p(p) = \frac{\epsilon_2 k_1 - \epsilon_1 k_2}{\epsilon_2 k_1 + \epsilon_1 k_2 + 2i\epsilon_2 k_1 k_2 \cot(k_2 a)}, \tag{S9}$$

where a is the thickness of the film.

Finite thickness effects have a significant impact on the noise power spectrum outside of the film. The distance and temperature dependence experiments, depicted in FIGS. 2 and 3, used films with thicknesses a=60 nm and a=100 nm, respectively. The theoretical predictions shown in those figures incorporate these finite-thickness corrections. Conversely, in the case of the single-crystal films, which are much thicker (a=1.5 μm), the corrections due to finite thickness are negligible.

Furthermore, in the experiments involving polycrystalline silver, an extra 5 nm layer of $SiO_2$ lies between the diamond and the metal. Such a geometry can also be accounted for with the appropriate reflection coefficients. However, because $\mu \approx 1$ in diamond and $SiO_2$, the length scales z and electromagnetic field wave vectors $|k|=\epsilon\omega/c$ such that $|k|z \gg 1$, and the electromagnetic response is dominated by $|\epsilon_2|=\epsilon_{Ag}\gg\{|\epsilon_{Diamond}|, |\epsilon_{SiO2}|\}$, the effects of the diamond medium and the silica layer are both negligible.

3.3 Quasi-Static Approximation

It is convenient to perform approximations to the integrals in equations (S2) and (S3) to gain insight into the decay rate behavior in different regimes. In particular, in the case of a full metallic half space, and in the regime where the electromagnetic wavelength is much larger than the skin depth of the metal, $\lambda \gg \delta$, and the skin depth is much larger than the spin's distance to the metal, $\delta \gg z$, $$S_B^x(z) = S_B^y(z) \approx \frac{\hbar\omega\sigma}{64\pi\epsilon_0^2 z} \tag{S10}$$

$$S_B^z(z) \approx 2S_B^r \tag{S11}$$

In this regime, known as the quasi-static regime, the decay rate, as described in equation (S1), is proportional to $1/z$, and thus $T_1 = 1/\Gamma \propto z$.

3.4 NV Magnetic Dipole Orientation

We also must account for the orientation of the magnetic dipole of our NV centers when calculating the expected decay rate. The decay rate from $|m_s=0\rangle$ to $|m_s=1\rangle$ for a spin-1 system with a quantization axis making an angle $\theta$ with $\hat{z}$, the vector normal to the metal surface, in the quasi-static limit is given by $$\gamma_{0\to 1} = \frac{1}{\hbar^2}\coth\left(\frac{\hbar\omega}{2k_B T}\right)\sum g^2\mu_B^2 |\langle 1|S_i|0\rangle|^2 S_B^i(z,\omega) \tag{S12}$$

$$\approx \frac{g^2\mu_B^2}{\hbar^2}\frac{2k_B T}{\hbar\omega}\left(\frac{1}{2}\cos^2(\theta)S_B^x(z,\omega) + \frac{1}{2}S_B^y(z,\omega) + \frac{1}{2}\sin^2(\theta)S_B^z(z,\omega)\right) \tag{S13}$$

$$\approx \frac{g^2\mu_B^2\mu_0^2 k_B T\sigma}{32\pi z\hbar^2}\left(1 + \frac{1}{2}\sin^2(\theta)\right). \tag{S14}$$

where in our temperature and frequency range of interest ($T > 4$ K and $\omega < 20$ GHz), $\coth(\hbar\omega/2k_B T) \approx 2k_B T/\hbar\omega$, and we choose our coordinate system such that the spin is always in the x-z plane. All diamond samples used in the experiment are cut such that all four possible NV dipole orientations make the same angle $\theta = \frac{1}{2}(180° - \cos^{-1}(\frac{1}{3})) \approx 54.7°$ with $\hat{z}$.

3.5 Three-Level System Dynamics

We also must account for the population dynamics of our three level spin-1 coupled to a magnetic noise bath. The rate equations for this system are given by $$\partial_t \begin{pmatrix} \rho_{00} \\ \rho_{-1-1} \\ \rho_{11} \end{pmatrix} = \begin{pmatrix} -2\gamma & \gamma & \gamma \\ \gamma & -\gamma & 0 \\ \gamma & 0 & -\gamma \end{pmatrix}\begin{pmatrix} \rho_{00} \\ \rho_{-1-1} \\ \rho_{11} \end{pmatrix}, \tag{S15}$$

which, for boundary conditions $\rho_{00}(t=0)=1$, give the solution $$\rho_{00}(t) = \tfrac{2}{3}\exp(-3\gamma t) + \tfrac{1}{3}. \tag{S16}$$

Thus, the population decay from the $m_s=0$ state is a factor 3 larger than the rate given by equation (S14), and we arrive at $$\Gamma \approx \frac{3\mu^2 g^2\mu_B^2 k_B T\sigma}{32\pi\hbar^2 z}\left(1 + \frac{1}{2}\sin^2\theta\right), \tag{S17}$$

which is equivalent to equation (2) given in the main text.

3.6 Non-Local Corrections to the Decay Rate

To take into account the ballistic nature of the electron motion in the silver, we introduce a non-local permittivity. In this regime we find $S_B^z \approx 2S_B^x$ still holds, so for simplicity in the discussion that follows we consider only $S_B^z$. With the Lindhard form modified for finite electron lifetime, the s polarized reflection coefficient becomes $$r^s(k_x, k_y) = \frac{\frac{2iqc^2}{\pi\omega^2}\int_0^\infty \frac{d\kappa}{\epsilon_t(k,\omega) - c^2 k^2/\omega^2} - 1}{\frac{2iqc^2}{\pi\omega^2}\int_0^\infty \frac{d\kappa}{\epsilon_t(k,\omega) - c^2 k^2/\omega^2} + 1}, \tag{S18}$$

with $k^2 = p^2 + \kappa^2$ and the transverse permittivity defined as $$\epsilon_t(k,\omega) = 1 - \frac{\omega_p^2}{\omega(\omega + i\nu)}f_t((\omega + i\nu)/k\nu_f), \tag{S19}$$

and the function $f_t$ defined as $$f_t(x) = \frac{3}{2}x^2 - \frac{3}{4}x(x^2 - 1)\ln\left(\frac{x+1}{x-1}\right), \tag{S20}$$

and $\omega_p$ is the electron plasma frequency, $\nu$ is the electron scattering rate, $\omega$ is the frequency of radiation, and $\nu_f$ is the Fermi velocity. In the above expressions, the non-locality manifests itself through the k dependence of the permittivity. In order to derive an analytical expression for $S_B^z$ in the limit $z \to 0$, we first rewrite the $S_B^z$ in terms of the rescaled, dimensionless momentum $\tilde{p} = (\nu_f/\nu)p$ and introduce $$\alpha = \frac{\nu}{w}\frac{c}{\nu_f}$$

$$S_B^z = \frac{\hbar}{4\pi\epsilon_0 c^2}\frac{\nu^3}{\nu_f^3}Re\int_0^\infty d\tilde{p}\frac{\tilde{p}^3}{\sqrt{1/\alpha^2 - \tilde{p}^2}}e^{i\frac{2\nu z}{\nu_f}\sqrt{1/\alpha^2 - \tilde{p}^2}}r^s(\tilde{p}) \tag{S21}$$

$$r^s(\tilde{p}) = \frac{2i\sqrt{1/\alpha^2 - \tilde{p}^2}\int_0^\infty \frac{d\tilde{\kappa}}{\epsilon_t/\alpha^2 - \tilde{p}^2 - \tilde{\kappa}^2} - \pi}{2i\sqrt{1/\alpha^2 - \tilde{p}^2}\int_0^\infty \frac{d\tilde{\kappa}}{\epsilon_t/\alpha^2 - \tilde{p}^2 - \tilde{\kappa}^2} + \pi}. \tag{S22}$$

In the regime of our interest $\alpha \sim 10^6$, we can replace $\sqrt{1/\alpha^2 + \tilde{p}^2}$ with $i\tilde{p}$ to good approximation. Also, by separating the real and imaginary parts of the numerator and the denominator of equation (S22), it can be shown that when $\nu/\omega \sim 10^3 \gg 1$, the imaginary part of $r^s$ is well-approximated by $$\text{Im}(r^s) \approx \frac{\tilde{p}}{\pi}\frac{1}{\alpha^2}\int_0^\infty \frac{\text{Im}(\epsilon_t)d\tilde{\kappa}}{(\tilde{p}^2 + \tilde{\kappa}^2)^2}. \tag{S23}$$

Finally, the substitution of equation (S23) into equation (S21) and the change of variables $\tilde{p} = r\cos(\theta)$, and $\tilde{\kappa} = r\sin(\theta)$, and $\tan(\varphi) = 1/r$ give us $$S_B^z = \frac{\hbar}{4\pi^2\epsilon_0 c^4}\frac{\omega_p^2\omega}{\nu_f}C(2\nu z/\nu_f) \tag{S24}$$

where the dimensionless function C(a) is given by $$C(a) = \int_0^{\pi/2}\int_0^{\pi/2} d\theta d\phi \frac{\cos^3(\theta)e^{-a\frac{\cos(\theta)}{\tan(\phi)}}}{\sin(\phi)\cos^2(\phi)} \frac{3}{2}\left(\frac{\pi/2-\phi}{\cos(\phi)}-\sin(\phi)\right). \quad (S25)$$

The function C(a) has a logarithmic divergence $$C(a) \approx -\frac{\pi}{2}$$

ln (a) in the limit a→0. This originates from integration over infinitely large momentum p in the integral in equation (S3). Therefore, we introduce a physical cut-off, which modifies the range of integration for φ from [0, π/2] to [φc, π/2] with tan $$(\varphi_c) \equiv \frac{v}{v f k_{cut}}.$$

Using $k_{cut}=2\pi/a_{Ag}$ with $a_{Ag}=0.4$ nm, the lattice spacing of silver, we obtain well-defined behavior in the limit z→0, $C_{cut}(2vz/v_f) \approx 4.6\pi$, which leads to Eq. 3.

4. Spectral Dependence of Johnson Noise

From equation (S17), it is clear that the noise spectrum of magnetic Johnson noise is white for frequencies over which coth $(\hbar\omega/2k_BT) \approx 2k_BT/\hbar\omega$. We verify this by applying an external magnetic field, B∥, along the NV axis to tune the NV spin transition frequencies $$\omega_\pm = \Delta + 2g\mu B B_\parallel/\hbar \quad (S26)$$

where $\omega_\pm$ denotes the transition frequency from the $|m_s=0\rangle$ to the $|m_s=\pm1\rangle$ states, Δ denotes the NV spin ground state zero-field splitting (2π×2.88 GHz), and gμB is the NV electronic spin magnetic moment. We measure the relaxation rate when the NV is initially polarized in the |0⟩ state, and when it is initially polarized in the |±1⟩ states. Based on the rate equations given in section 1.2 (equation (S15)), the population relaxation from the |0⟩ state is given by equation S16, while the population relaxation from the |±1⟩ state takes the following form:

$$\rho_{\pm1\pm1}(t) = \frac{1}{6}e^{-3\gamma t} + \frac{1}{2}e^{-\gamma t} + \frac{1}{3}. \quad (S27)$$

Figure 9:
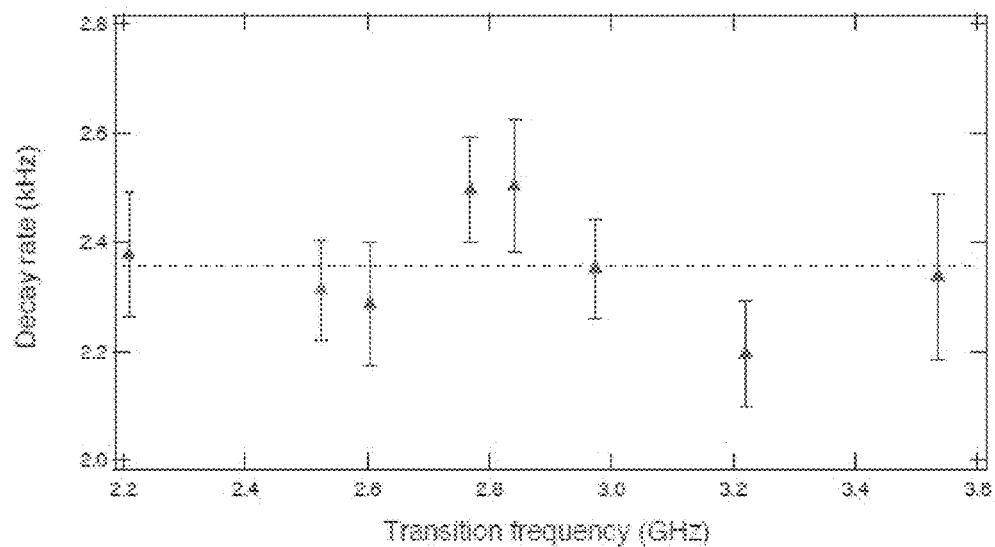
FIG. 9 shows Johnson noise spectral dependence according to one or more embodiments in which static magnetic fields are applied to shift the NV spin transition frequencies; and when polarized in the |±1) state, the relaxation rate of the NV center is sensitive to the magnetic field noise at the frequency ω±given by Eq. S26 (The red triangle corresponds to the decay rate extracted from the data shown in FIG. 1D.).

We observe excellent agreement with these predictions, and simultaneously fit to the relaxation from the |0⟩ and |±1⟩ states with only a single decay rate γ. A representative data set and fit are shown in FIG. 1D. The extracted rates γ at different magnetic fields, and therefore different NV transition frequencies, are shown in FIG. 9. We find good agreement with the hypothesis of a white noise bath, with $\chi^2/N=0.87$, for the ω=2π×2.2-3.6 GHz range.

5. NV $T_1$ Statistics

For NVs implanted at shallow depth such as the ones used in this work, we occasionally observe short NV $T_1$ times for NVs under bare diamond (see Table 1). The origin of the fast decay is unclear. No spatial correlations in T1 are observed for the NVs with reduced $T_1$ times.

TABLE 1

$T_1$ statistics for 16 of the NVs shown in FIG. 4 (corresponding to the blue triangles in FIG. 11D), in the absence of silver.

| Number of NVs | $T_1$ |
|---|---|
| 13 | ≥2 ms |
| 1 | 1.2 ms |
| 1 | 500 μs |
| 1 | 300 μs |

5.1 Extraction of Relaxation Rates and Distances Under Polycrystalline Silver

Figure 10:
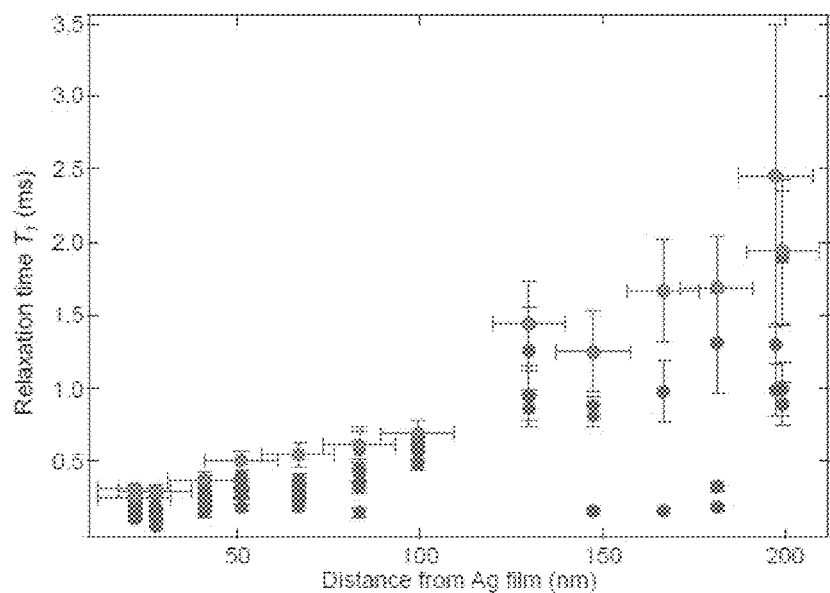
FIG. 10 shows T1 vs distance to the film in which the distance from NVs to the silver surface is varied via a gradual silica ramp (~15-200 nm over ~1.5 mm), and the measured NV T1 times are plotted as a function of distance to the film in each region; the maxima, corresponding to the data shown in FIG. 2B, are plotted in red, and data from all other measured NVs is plotted in blue.

Due to the variability in NV $T_1$ times under bare diamond, when measuring under silver a spread in the $T_1$ times of the NVs is observed, as shown in FIG. 10, especially at larger distances from the silver, consistent with the variation observed on bare diamond. This is because the Johnson noise only sets an upper limit on the NV spin lifetime, and other local sources of noise can still reduce it further. To compensate for this 5-10 NVs at each point along the ramp were measured, such that the maximum $T_1$ observed in at each point is Johnson noise limited (10 NVs per points were measured for the 7 closest points measured from 20-80 nm, and 5 NVs per points for the other 7 points, from 100-200 nm). Only NVs with a spin-dependent fluorescence contrast within the expected range of 15-35% were included. The result is plotted in FIG. 10. The data plotted in FIG. 2 is the inverse of the maximum $T_1$ measured at each point along the ramp (the red data points in FIG. 10.)

In the theoretical prediction for the distance-dependent relaxation rate shown in FIG. 2, a correction to the lifetime predicted by equation (Si) was included to account for the phonon-induced NV spin relaxation at room temperature, $T_1^{ph}=6$ ms, consistent with measured $T_1$ times under bare diamond. This is a significant correction only at larger distances from the film and only at room temperature and has a negligible impact on the measurements and analysis presented in all other figures.

When estimating the distance to the film for the NVs plotted in FIG. 2, the largest source of error is the variation in depth below the surface of the implanted NVs. As a result, the statistical bias in NV depth introduced by selecting the maximum $T_1$ in each region is also accounted for. In particular, as most NVs have Johnson noise limited lifetimes, by taking the maximum $T_1$ measured we are likely selecting not only for an NV with a $T_1$ limited by Johnson noise, but also for the deepest NV in each region. To account for this, we assume the NV implantation depths are normally distributed, with a mean depth μ=15 nm and a standard deviation σ=10 nm. Let $N_{\mu,\sigma}(x)$ denote the normal distribution representing the NV depth profile. If n NVs are randomly selected from this distribution, it can be shown that the probability the deepest NV selected has depth x is given by $$P_{max}(x) = n\left(\int_{-\infty}^x N_{\mu,\sigma}(x')dx'\right)^{n-1} N_{\mu,\sigma}(x). \quad (S28)$$

This new distribution is used to determine the expected value and standard deviation of the depth of the NV selected at each point along the ramp. For example, if n=5 NVs are measured at one point along the ramp, from the above probability distribution function $P_{max}$, the expected value for the depth of the deepest NV measured is 27 nm with a standard deviation of 7 nm, while at a point where n=10 NVs are measured the likely distribution of depths is 30±6 nm. These depths are then added to thickness of the ramp at that point to give the total distance to the silver surface plotted in FIG. 2.

Figure 3A:
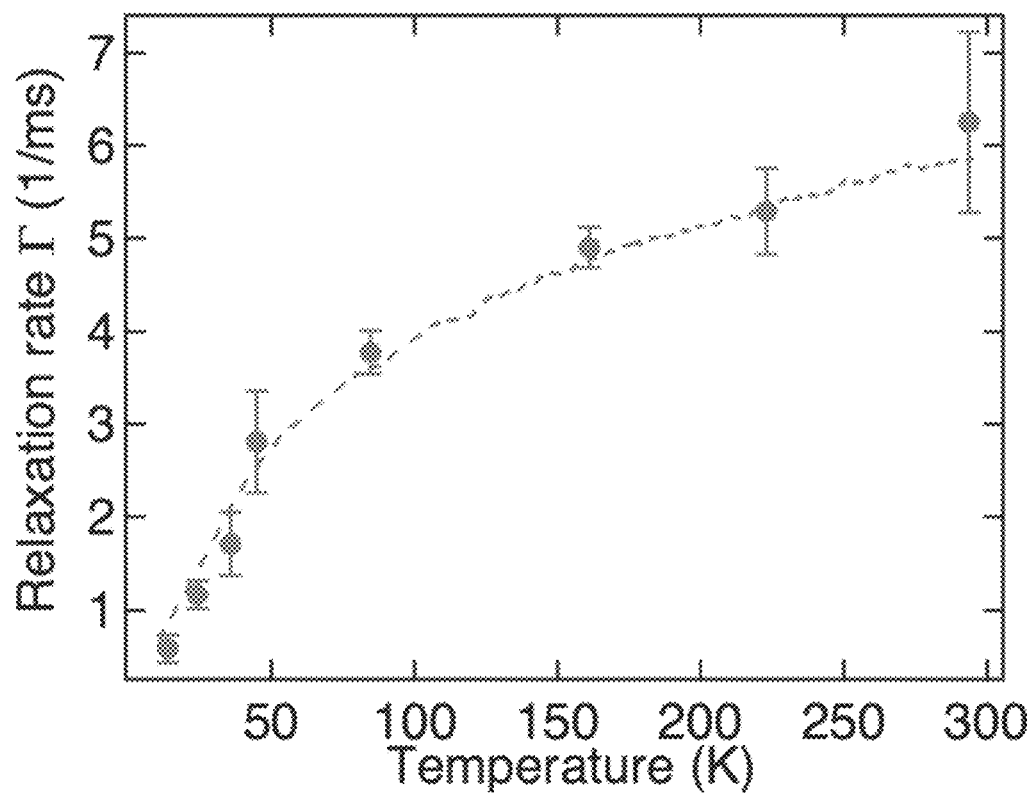
FIG. 3A illustrates the measured relaxation time $T_1$ of single NV spin under a polycrystalline silver film as a function of temperature (red data points). The conductivity of the silver film as a function of temperature shown in FIG. 3B, shown later, is included in a fit to Equation 2, with the distance to the film as the single free parameter (red dashed line)

In the temperature-dependence measurements shown in FIG. 3A, an NV-film distance of d=31±1 nm is extracted from the fit to equation (2). This is consistent with expectations, as a depth 15±10 nm from implantation parameters, in addition to the 5-nm thick $SiO_2$ spacer layer, is expected.

5.2 NVs Under Single-Crystal Silver

In total, the $T_1$ of 25 NVs close to the single-crystal silver sample were measured at 12 temperatures, in three different spatial regions on the sample. Each region was 40 μm×40 μm in size, and the regions were each spatially separated from each other by more than 100 μm. Of the 25 measured NVs, 16 were in region A (blue triangles in FIG. 11D), where the diamond surface was observed to be in contact with the silver, 7 were in region B where a gap was expected to be growing between the diamond and the silver (pink squares in FIG. 11D), and 2 were in region C, where the gap was expected to be fairly large (gray circles in FIG. 11D).

The gap between the diamond and silver was qualitatively apparent based on a number of separate observations. A variation in the brightness of the NVs is observed in the different regions when exposed to the same laser power at the objective, which we attribute primarily to optical interference coming from the reflections off the silver and diamond surfaces. In addition, we measured reduced NV optical excited state lifetimes in region A (the region in contact with silver) which is attributed to quenching from the silver (see Table 2). An accumulation of a small amount of fluorescent background on the diamond surface is also observed over time in regions B and C, which was absent from region A, as would be expected if the diamond and silver were in direct contact there.

TABLE 2

Figure 11A:
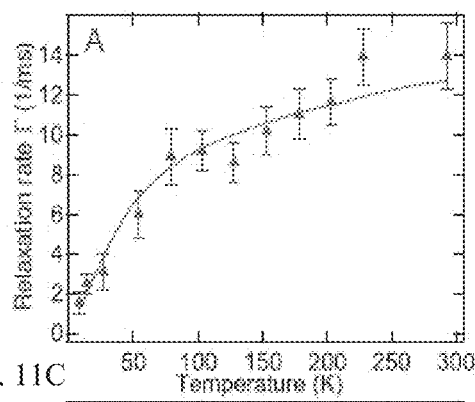
Figure 11B:
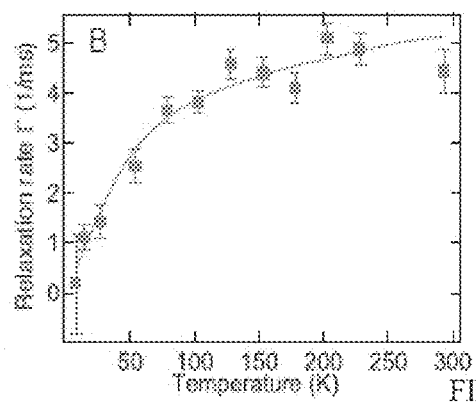
Figure 11C:
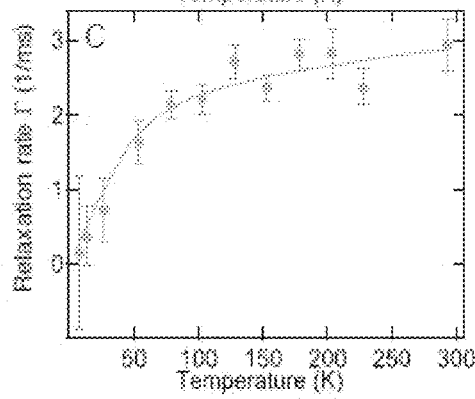
Figure 11D:
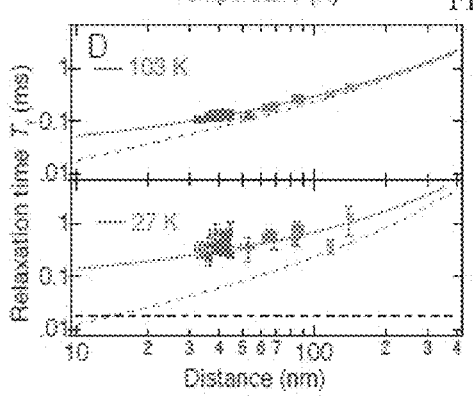

Mean optical excited state lifetimes by spatial region for the NVs show in FIG. 4 of the main text and FIG. 11D

| Region | Mean excited state lifetime |
| --- | --- |
| A | 8.2 ns |
| B | 12.5 ns |
| C | 13.6 ns |

The $T_1$ time at room temperature of all 25 NVs was also subsequently measured after the silver sample was removed. Of these NVs, one NV in region A was rejected because the measured $T_1$ times under silver were not repeatable, and one NV in region B was rejected because it had very short $T_1$ times even at low temperatures (<300 μs at 8 K) leaving 23 NVs that compose the dataset shown in FIG. 4D and FIG. 11D).

Those skilled in the art would readily appreciate that all parameters and configurations described herein are meant to be exemplary and that actual parameters and configurations will depend upon the specific application for which the systems and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that the invention may be practiced otherwise than as specifically described. The present invention is directed to each individual feature, system, or method described herein. In addition, any combination of two or more such features, systems or methods, if such features, systems or methods are not mutually inconsistent, is included within the scope of the present invention.

What is claimed is:

1. A method of making measurements, comprising:
   providing a sensor with at least one solid state electronic spin;
   irradiating the sensor with radiation from an electromagnetic radiation source that manipulates the solid state electronic spins to produce spin-dependent fluorescence,
       wherein the spin-dependent fluorescence decays as a function of relaxation time;
   providing a target material in the proximity of the sensor,
       wherein, thermally induced currents (Johnson noise) present in the target material alters the fluorescence decay of the solid state electronic spins as a function of relaxation time; and
   determining a difference in the solid state spins spin-dependent fluorescence decay in the presence and absence of the target material and correlating the difference with a property of the sensor and/or target material.

2. The method of claim 1, wherein the property of the target material measured is localized at a length scale of 10-100 nm.

3. The method of claim 2, wherein the property measured is the resistance values within the target material.

4. The method of claim 2, wherein the property measured is the temperature of the target material.

5. The method of claim 1, wherein the property measured is the distance of the target material from the surface of the sensor.

6. The method of claim 1, wherein the property measured is the distance of the solid state electronic spins from the surface of the sensor.

7. The method of claim 1, wherein, the sensor comprises a diamond crystal lattice.

8. The method of claim 7, wherein, the solid state electronic spins comprises a defect in the diamond crystal lattice.

9. The method of claim 8, wherein the defect comprises a nitrogen vacancy center in a diamond crystal lattice.

10. The method of claim 1, wherein, the electromagnetic radiation source is a laser.

11. The method of claim 1, wherein, the laser source emits a laser having wavelength of about 532 nanometers.

12. The method of claim 1, wherein the target material is in contact with the sensor.

13. The method of claim 1, wherein the target material is not in contact with the sensor.

14. The method of claim 1, wherein the target material is a conductive material.

15. The method of claim 1, wherein the target material is a metal.

16. The method of claim 1, wherein the target material is silver.

17. The method of claim 1, wherein the target material is copper.

18. The method of claim 1, wherein the target material is a single crystal.

19. The method of claim 18, wherein the single crystal is a silver single crystal.

20. The method of claim 1, wherein the target material is polycrystalline.

21. The method of claim 1, wherein the target material is a conductive polymer.

* * * * *

UNITED STATES PATENT AND TRADEMARK OFFICE
CERTIFICATE OF CORRECTION

| | | |
|---|---|---|
| PATENT NO. | : 10,197,497 B2 | Page 1 of 1 |
| APPLICATION NO. | : 15/547092 | |
| DATED | : February 5, 2019 | |
| INVENTOR(S) | : Shimon Jacob Kolkowitz et al. | |

It is certified that error appears in the above-identified patent and that said Letters Patent is hereby corrected as shown below:

In the Specification

The paragraph titled "STATEMENT OF GOVERNMENT RIGHTS" in Column 1, beginning at Line number 12 Should Read:
This invention was made with government support under Grant No. HR0011-111-C-0073 awarded by the Department of Defense/Defense Advanced Research Projects Agency; 0969816 and 1125846 awarded by the National Science Foundation; and 6927102 awarded by the U.S. Army Research Office. The government has certain rights in this invention.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*